(12) United States Patent
Fergenson

(10) Patent No.: US 8,373,858 B2
(45) Date of Patent: Feb. 12, 2013

(54) SYSTEM AND METHOD FOR REAL TIME DETERMINATION OF SIZE AND CHEMICAL COMPOSITION OF AEROSOL PARTICLES

(75) Inventor: David Philip Fergenson, Alamo, CA (US)

(73) Assignee: Livermore Instruments, Inc., Dublin, CA (US)

( * ) Notice: Subject to any disclaimer, the term of this patent is extended or adjusted under 35 U.S.C. 154(b) by 340 days.

(21) Appl. No.: 12/618,716

(22) Filed: Nov. 14, 2009

(65) Prior Publication Data

US 2011/0116090 A1      May 19, 2011

Related U.S. Application Data

(60) Provisional application No. 61/121,494, filed on Dec. 10, 2008.

(51) Int. Cl.
*G01N 15/02* (2006.01)
*G01N 21/00* (2006.01)

(52) U.S. Cl. ......... 356/335; 356/336; 356/337; 356/338

(58) Field of Classification Search ........... 356/332–343
See application file for complete search history.

(56) References Cited

U.S. PATENT DOCUMENTS

| | | | | |
|---|---|---|---|---|
| 4,457,624 A | * | 7/1984 | Goldberg et al. | 356/336 |
| 4,919,536 A | * | 4/1990 | Komine | 356/28.5 |
| 4,938,592 A | * | 7/1990 | Poole et al. | 356/335 |
| 5,266,798 A | * | 11/1993 | Borden et al. | 250/239 |
| 5,395,588 A | | 3/1995 | North et al. | |
| 5,606,418 A | * | 2/1997 | Borden et al. | 356/364 |
| 5,637,881 A | * | 6/1997 | Burghard et al. | 250/573 |
| 5,681,752 A | | 10/1997 | Prather | |
| 5,861,950 A | * | 1/1999 | Knowlton | 356/338 |
| 6,959,248 B2 | | 10/2005 | Gard et al. | |
| 7,260,483 B2 | | 8/2007 | Gard et al. | |
| 2005/0073683 A1 | * | 4/2005 | Gard et al. | 356/337 |

OTHER PUBLICATIONS

Daniel M. Murphy, The Design of Single Particle Laser Mass Spectrometers; Published online Oct. 16, 2006 in Wiley InterScience (www.interscience.wiley.com) DOI 10.1002/mas.2.

* cited by examiner

*Primary Examiner* — Michael P Stafira
(74) *Attorney, Agent, or Firm* — Douglas Baldwin

(57) ABSTRACT

This invention is an apparatus and method of real time determination of particle size and optionally chemical composition or both. An aerosol beam generator focuses a beam containing sample particles that passes through a sizing laser beam of approximately constant width to produce light scattering that is detected by a light detection means, allowing generation of electrical pulses that may be used to compute particle velocity. In being formed into a beam, the particles are accelerated to terminal velocities that are functions of their sizes. The duration of time elapsed while a particle passes through the width of the sizing laser beam is a function of its velocity which, in turn, is a function of its size. Chemical composition of the particle is determined by suitable analytical means included in the apparatus, such as mass spectrometry.

18 Claims, 5 Drawing Sheets

Figure 1:
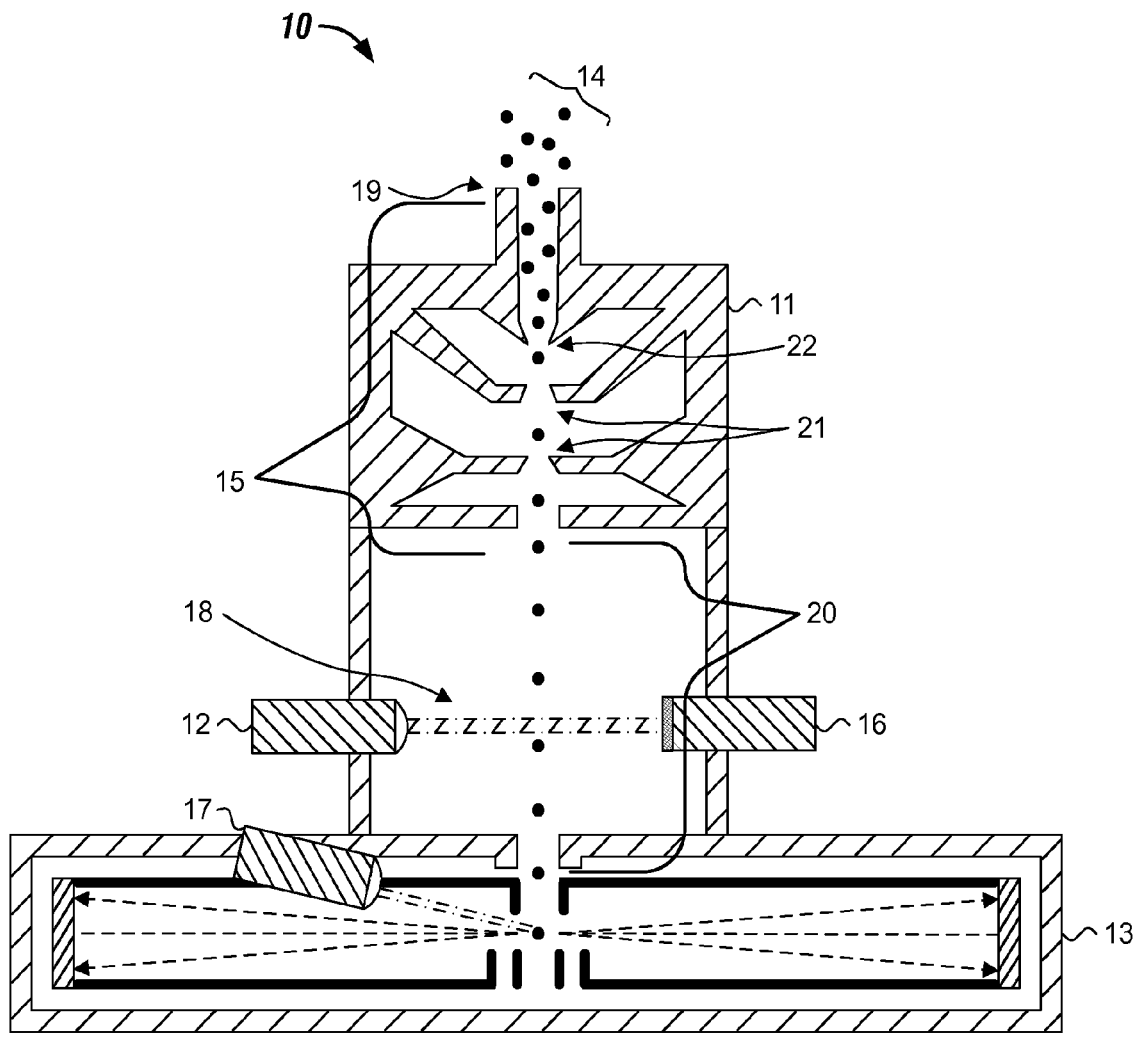

```
60 ─▶
    ┌─────────────────────────┐
    │   Generate aerosol beam │ ～ 61
    └───────────┬─────────────┘
                ▼
    ┌─────────────────────────┐
    │ Determine particle      │ ～ 62
    │ velocity and size       │
    └───────────┬─────────────┘
                ▼
    ┌─────────────────────────┐
    │   Detect Mass Spectra   │ ～ 63
    └───────────┬─────────────┘
                ▼
    ┌─────────────────────────┐
    │     Analyze Spectra     │ ～ 64
    └───────────┬─────────────┘
                ▼
    ┌─────────────────────────┐
    │     Identify particle   │ ～ 65
    └─────────────────────────┘
```

Fig. 6

```
70 ─▶
    ┌─────────────────────────┐
    │    Detect light scatter │ ～ 71
    └───────────┬─────────────┘
                ▼
    ┌─────────────────────────┐
    │ Detect lack of light scatter │ ～ 72
    └───────────┬─────────────┘
                ▼
    ┌─────────────────────────┐
    │ Determine particle velocity │ ～ 73
    └───────────┬─────────────┘
                ▼
    ┌─────────────────────────┐
    │  Determine particle size │ ～ 74
    └─────────────────────────┘
```

Fig. 7

SYSTEM AND METHOD FOR REAL TIME DETERMINATION OF SIZE AND CHEMICAL COMPOSITION OF AEROSOL PARTICLES

CROSS REFERENCE TO RELATED APPLICATIONS

This application claims the benefit of U.S. Provisional Application No. 61/121,494 filed Dec. 10, 2008.

FIELD OF THE INVENTION

The invention relates to aerosol particle identification and, in particular, to a system and method for real time determination of size and optionally the chemical composition of aerosol particles.

BACKGROUND

A rise in concern over terrorism has increased interest in real time detection and identification of aerosol particles, as radiological, chemical, biological, and explosive materials and their precursors can all be found in aerosolized form.

Recent advances in aerosol mass spectrometry enable real time analysis of aerosol particles in the field, critically important at high value terrorism targets, such as centers of government, airports, and sports venues. Aerosol mass spectrometry requires conditioning the aerosol under analysis, forming a particle beam, and analyzing individual particles by laser desorption/ionization mass spectrometry. Conditioning can include generating the aerosol, if the particles are not already aerosolized, and adjusting the concentration of particles. A particle beam is formed by the supersonic expansion of the gas surrounding the particles through focusing apertures. Particles in a liquid stream may similarly be formed into a beam. Individual particles in the particle beam are then analyzed by mass spectrometry.

Dense particle concentrations can adversely impact the ability of aerosol mass spectrometers to accurately track, resolve, and analyze individual particles. Inaccurate velocity measurement can skew the timing necessary for precise actuation of an ionizing laser. Further, resolving high particle density has historically taken increased complexity and expense.

For instance, the rapid single particle spectrometer (RSMS), disclosed in McKeown et al., "On-Line Single Particle Analysis by Laser Desorption Mass Spectromerty," 63 Anal. Chem. 1906, 2069 (1991), the disclosure of which is incorporated by reference, utilizes a continuous wave laser for detecting the presence of a particle within an aerosol beam. Each particle scatters light while crossing a continuous laser beam. A photomultiplier tube (PMT) measures light scattering intensity to provide an approximate measure of particle size using the particle's reflective index, an inherently inaccurate size measurement. A pulsed laser is aimed adjacent to the continuous laser beam and is actuated upon detection of the particle. A mass spectrum is collected from material desorbed/ionized from the particle.

An aerosol time-of-flight mass spectrometer (ATOFMS), disclosed in U.S. Pat. No. 5,998,215, issued to Prather et al., the disclosure of which is incorporated by reference, sizes aerosol particles based on estimated velocity. Particle traversal time over the distance spanned by two continuous lasers is measured and extrapolated to trigger actuation of a mass spectrometer pulsed laser. Particle velocity yields more accurate particle size determination than does light scattering intensity, but the ability to track individual particles suffers as aerosol concentration increases, thereby limiting analytic throughput. Additionally, utilization of two lasers increases complexity over single laser designs.

An aerosol mass spectrometer system employing an array of six continuous lasers is disclosed in U.S. Pat. No. 7,260,483, issued to Gard et al., the disclosure of which is incorporated by reference. Throughput is improved by using a six-laser array to track the trajectories of individual aerosol particles. Higher performance at increased particle concentrations is achieved, but at the expense of size, cost, and complexity.

SUMMARY

Aerosol particle size and optionally composition are determined in real time for particle identification. An aerosol beam generator focuses an aerosol beam that contains an aerosol sample. Once at terminal velocity, each particle intersects a laser beam of known constant width emitted from a continuous wave sizing laser. Particle traversal time through the sizing laser's beam is measured edge-to-edge and used to determine particle velocity, from which particle size can then be estimated. In one embodiment a pulsed laser desorbs and ionizes the particle for spectral analysis. In another aspect, the identity of the particle is determined from analysis of the particle size and composition.

Still other embodiments will become readily apparent to those skilled in the art from the following detailed description, wherein are described embodiments by way of illustrating the best mode contemplated. As will be realized, other and different embodiments are possible and their several details are capable of modifications in various obvious respects, all without departing from the spirit and the scope. Accordingly, the drawings and detailed description are to be regarded as illustrative in nature and not as restrictive.

BRIEF DESCRIPTION OF THE DRAWINGS

FIG. 1 is a functional block diagram showing a system for determining size and chemical composition of individual aerosol particles in accordance with one embodiment.

FIG. 2 is a functional diagram showing, by way of example, real time determination of size and chemical composition of aerosol particles.

FIGS. 3A-C are block diagrams showing, by way of example, a particle traversing the sizing laser beam of the system of FIG. 1.

FIG. 4 is a block diagram showing path lengths through a circular shaped laser beam and square shaped laser beam.

FIG. 5 is a graph showing an exemplary particle-size-to-particle-velocity calibration curve.

FIG. 6 is a flow diagram showing a method for determining the size and chemical composition of individual aerosol particles in accordance with one embodiment.

FIG. 7 is a flow diagram showing the routine for determining the velocity and size of the particle for use in the method of FIG. 6.

DETAILED DESCRIPTION

Efficient and accurate identification of potentially hazardous aerosol particles is vital for protection of public safety and most efficacious when performed in real time. More generally there is a need for rapid, adequate and efficient identification of a variety of microscopic particles, such as bacteria, viruses and the like. The present invention provides apparatus and method for accomplishing those needs.

FIG. 1 is a functional block diagram showing a system 10 for determining size and chemical composition of individual aerosol particles in accordance with one embodiment. By way of overview, for particle identification, the system 10 includes an aerosol beam generator 11, an aerosol particle sizing laser 12, and a mass spectrometer 13. Other components may be included and additional functions are possible, including aerosol generation, data visualization, analysis, and offload.

The system 10 is constructed in a rugged, highly transportable form that allows efficient deployment to sites in the field for a wide variety of uses, such as counter bioterrorism, environmental studies, or basic research. The simple design results in a system that is less complex to use and maintain, less expensive to produce, and more efficient than other systems employing large laser arrays. Use of a single continuous wave laser for particle tracking eliminates the complexity of systems that use multiple lasers, while retaining particle sizing accuracy based on particle velocity. Simplifying the system reduces the additional components and electronics required by other machines, allowing for a more reliable system that is less complicated to set up, transport, and tune. Additionally, reducing the length of distance and time that the particle beam must remain focused allows for greater throughput and reduces instrumental artifacts.

In general, aerosol particles 14, for analysis by the system 10, can be collected directly from ambient open air through real time sampling or indirectly from a contained air sample. Additionally, aerosol particles 14 can be produced from a test specimen, for example, by blowing compressed air across the specimen or directly aerosolizing the specimen using a nebulizer or similar laboratory instrument. A conduit (not shown), such as a duct or pipe, connects the source of aerosol particles 14 to the system 10. Aerosol particles 14 are thus first introduced into the system 10 through an inlet 19 of the aerosol beam generator 11.

The aerosol beam generator 11 collimates the particles 14 into an aerosol beam 15. The aerosol beam generator 11 can be an aerodynamic focusing lens stack, such as disclosed in U.S. Pat. No. 5,270,542, issued to McMurry et al., the disclosure of which is incorporated by reference. The principal requirement is that the beam generator be capable of producing a high speed narrow focused beam of particles from an aerosol (or liquid) sample that may be directed past a sizing laser beam. Thus other aerosol beam generators, the choice of which is well within the skill of the art can be used to form an aerosol beam 15 of suitable density and velocity. In one embodiment, the particles 14 are focused into the aerosol beam 15 through successively smaller apertures (omitted for clarity) and accelerated by a converging conical nozzle 22. Skimmers 21 allow the aerosol beam 15 to proceed between them but allow successively higher vacuums to be achieved as gas is evacuated from the system 10 in each chamber between them. Particles 14 from the evacuated aerosol beam 15 remain and travel as a focused particle stream 20 further downstream through the system 10.

At the terminus of the path, the aerosol beam generator 11 produces a particle stream 20 with a narrow focused cross section. A differential decrease in manifold pressure within the aerosol beam generator 11 causes supersonic expansion of the gas containing the particles 14 while in transit, while the apertures focus the particles 14 into a concentrated particle stream 20 that exits the aerosol beam generator 11 at supersonic velocity, such that the particles 14 diverge slowly from the beam axis due to acquired inertia. The velocity of the particles is a direct function of size, and therefore for each specific system, measurement of the terminal velocity of the particles is used to determine size of the particle.

Downstream, the particle stream 20 passes through a continuous wave laser beam 18 generated by a sizing laser 12 to determine the velocity of individual particles 14. Particle velocity is determined from the length of time which a particle needs to transit across the cross section of the beam 18, as discussed below in further detail with reference to FIG. 3. Particle velocity can then be used to determine the size of an individual particle 14. In one embodiment, particle size is determined from a particle-velocity-to-size calibration curve as discussed in further detail below with reference to FIG. 5. Other means of estimating particle size from particle velocity are possible, for example, in the form of a table or cross-reference list.

The sizing laser 12 is oriented so the emitted laser beam 18 strikes the aerosol beam 15 downstream from the aerosol beam generator 11. Orthogonally to the axis of the aerosol beam 15, a particle 14 passing through the laser beam 18 interrupts the beam 18 and causes a pulse of scattered light, which is detected by the PMT 16. In one embodiment, the laser beam 18 has multiple facets and is configured with two parallel faces of the beam 18 intersecting the aerosol beam 15. A particle 14 thus crosses both faces of the laser beam 18. An exemplary sizing laser 12 is a Blue Point 430/490 Laser, manufactured by Rainbow Photonics, Zurich, Switzerland, which generates a 430 nm wavelength laser, with a power output of 10 mW. A light detection means, such as a PMT 16, receives the continuous wave laser beam. Other sizing lasers and light detection sources could be used.

In a further embodiment, a minor or prism (not shown) is used in combination with the sizing laser 12 and PMT 16 to increase the efficiency of light detection. Light scattered by a particle could be undetected by the PMT 16. An ellipsoidal mirror with one focal point, for instance, positioned at the intersection of the laser beam 18 and the aerosol beam 20 and the other focal point on the surface of PMT 16, directs light for detection which may otherwise be lost and miss detection.

The PMT 16 converts sensed scattered light into an electric pulse that is provided to a timing circuit (not shown). The data-sampling rate of the electric pulses is sufficiently high to allow detection of the individual times at which the particle 14 enters and exits the laser beam 18. In one embodiment, electric pulses from the PMT 16 are collected at a sampling rate of 25 MHz, though lower or higher sampling rates could be used, depending on the velocity of the particles in the aerosol beam 15 and the precision desired.

Particle velocity is used to time the initiation of analysis by the mass spectrometer 13. The velocity of each particle 14 can be determined from the residence time of the particle 14 in the laser beam 18 generated by the sizing laser 12, which is dependent on the width of, or path length through, the beam, as discussed further below with reference to FIG. 3.

In a further embodiment, operation of the mass spectrometer can be initiated prior to determination of particle velocity, provided the ionizing laser is immediately adjacent to the sizing laser 12. Once light scattering is no longer detected by the PMT 16, which indicates that the particle 14 no longer resides in the laser beam, a signal from the timing circuit is sent to initiate the mass spectrometer 13, thereby avoiding the delay attendant to calculating particle velocity.

The particle stream 20 travels downstream from the sizing laser 12 into the ion source region of the mass spectrometer 13, where each particle 14 is desorbed and ionized by a pulsed desorption/ionization laser 17, such as a DS Series Deep UV Diode-Pumped Solid State Laser, manufactured by Photonics Industries Intl, Inc., Bohemia, N.Y., which produces a 263 nm wavelength laser, with a 3.0 watt average power output at its maximum rate of repetition. In addition the desorption/ionization laser 17 can be located adjacent to the sizing laser 12 to facilitate maintenance.

The spectra formed through particle desorption and ionization are analyzed by the mass spectrometer 13, which is either a monopolar time-of-flight mass spectrometer or, preferably, a bipolar time-of-flight mass spectrometer, such as a Z-TOF manufactured by Torwerk AG, Thun, Switzerland. Once collected, mass spectral data of the particle 14 can be electronically stored or imported into a spectral analysis computer program for further analysis. In one embodiment, spectral analysis is performed using commercial off-the-shelf software and executing on a computer system. The computer system is a general purpose, programmed digital computing device consisting of a central processing unit (CPU), random access memory (RAM), non-volatile secondary storage, such as a hard drive or CD ROM drive, network interfaces, and peripheral devices, including user interfacing means, such as a keyboard and display. Program code, including software programs, and data are loaded into the RAM for execution and processing by the CPU and results are generated for display, output, transmittal, or storage.

The analysis program analyzes the particle's spectral data, in combination with the particle size determined, to identify the chemical composition and identity of the particle 14. An exemplary method of spectral analysis is disclosed in U.S. Pat. No. 7,260,483, issued to Gard et al, the disclosure of which is incorporated by reference. Other modes of spectral analysis are possible.

Although the described system is configured for analyzing particles 14 suspended in a gas, the system can be easily adapted to analyzing particles suspended in aqueous or other liquid suspensions. For example, particles suspended in a liquid stream can be analyzed by a similar instrumental timing circuit in flow cytometry. Cytometers are described in U.S. Pat. No. 5,395,588, issued Mar. 7, 1995. The fluidics system of commercially available flow cytometers can be adapted as substitutes for the aerosol beam generator used for gas aerosols. As in aerosol beam generators, samples are injected into a core of a narrowing tube surrounded by a sheath with fast flowing fluid. Where the sheath fluid meets the tip of the injection core a fast moving stream of single particles is formed. The sizing laser and associated photo or light detector(s) are placed downstream as in the aerosol particle stream. Analytical means may also be used for particles in liquid suspension but not the mass spectrometric analysis used for aerosol particles. Selection of other suitable analytical means is well within the skill of those in the art.

Figure 2:
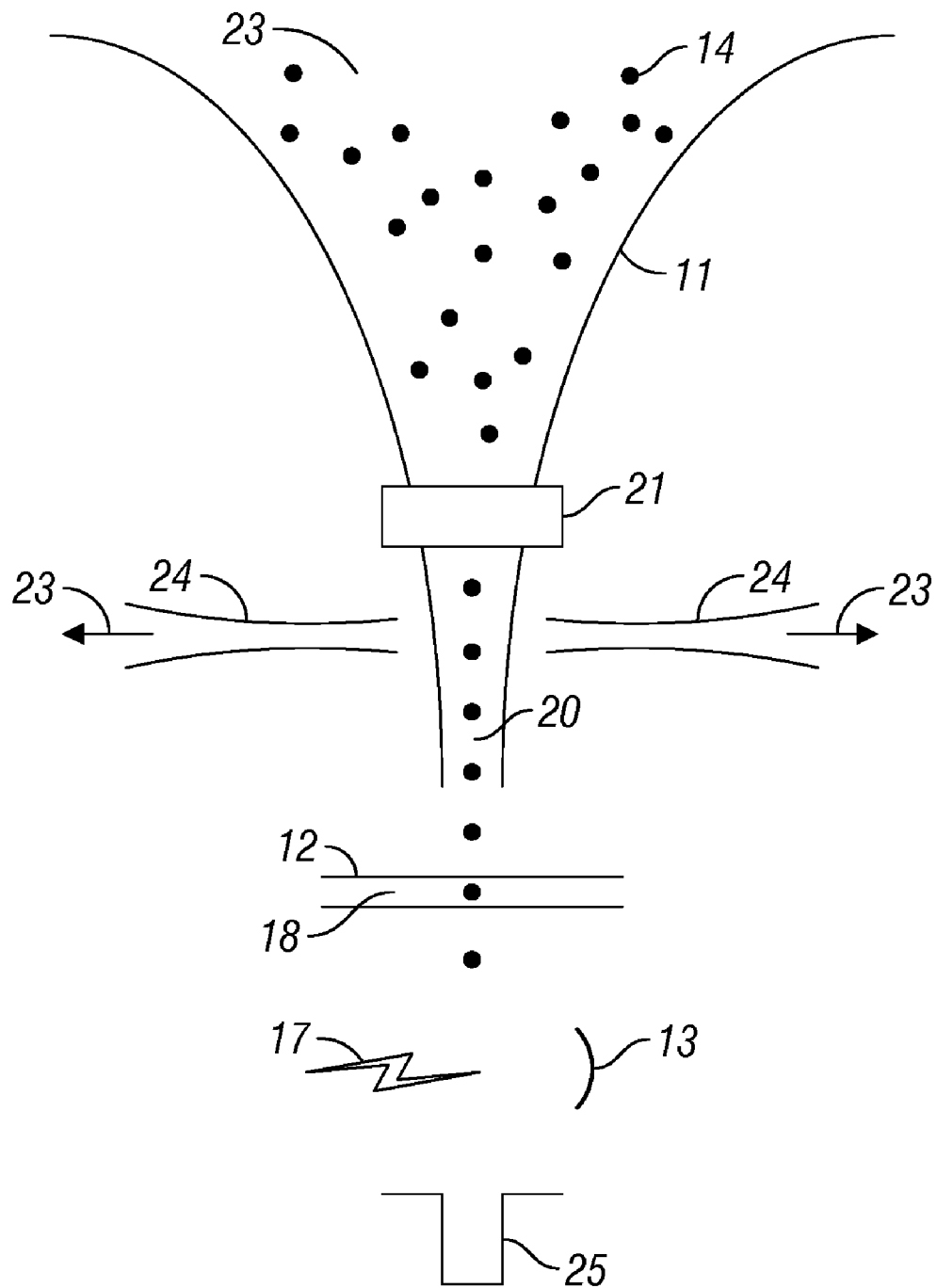

Aerosol particles 14 are focused into a narrow beam for individual analysis. FIG. 2 is a functional diagram showing, by way of example, real time determination of size and chemical composition of aerosol particles. A heterogeneous mixture of gas, 23, and aerosolized particles, 14, is introduced into the system via an inlet of an aerosol beam generator 11. The aerosol beam generator 11 accelerates the surrounding gas and suspended particles to supersonic speed through differential pressure created by a vacuum source 25. The terminal speed or velocity of the particles in the particle beam is a direct function of their size. The aerosolized particles are focused into an aerosol beam through one or more apertures. The surrounding gas 23 is evacuated from the system at point 24 leaving the particles 14 traveling downstream at speed as a focused particle beam 20. The aerosol beam generator 11 can be an aerodynamic focusing lens stack, as disused further above with reference to FIG. 1. Other aerosol beam generators are possible.

A sizing laser 12 is located downstream from the aerosol beam generator 11 and oriented such that the emitted laser beam 18 intersects the particle beam 20. Light scattering from a particle 14 crossing the laser beam is detected, 16, and used to determine particle velocity. Sizing of an individual particle 14 is estimated from its velocity, as discussed further below with reference to FIG. 5.

A desorption/ionization laser 17 is located downstream from the sizing laser 12. The desorption/ionization laser 17 emits a laser beam that ionizes and desorbs each particle 14 for analysis by a mass spectrometer 13. In one embodiment, the velocity of a particle is used for timing of actuation of the desorption/ionization laser 17. In a further embodiment, the desorption/ionization laser 17 is actuated when light scattering is no longer detected, while particle velocity is separately determined. Results of the spectral analysis and particle sizing are used to identify each particle 14.

Figure 3A:
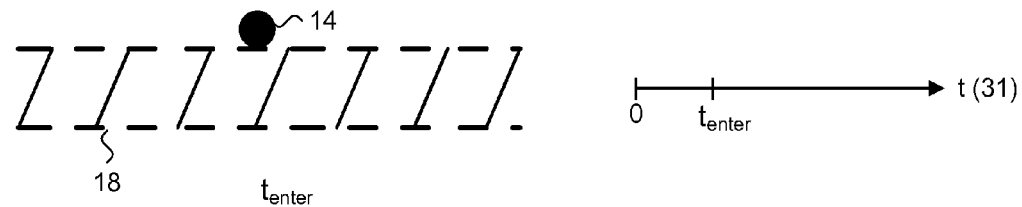
Figure 3B:
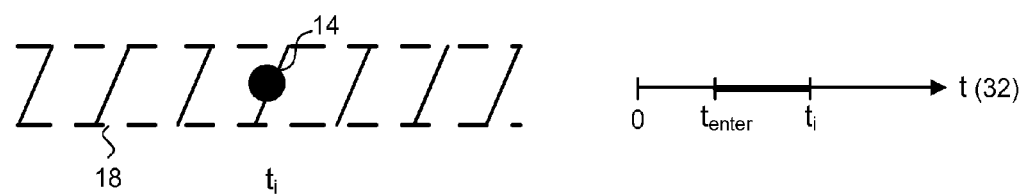
Figure 3C:
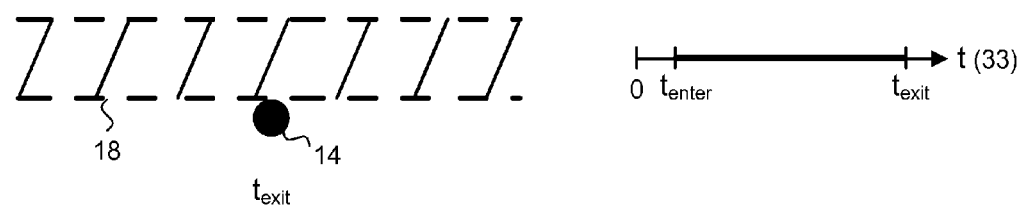

Particle velocity is determined and size is estimated from the residence time of a particle 14 when traveling through a sizing laser beam with a known path length. FIGS. 3A-C are block diagrams showing, by way of an example, a particle traveling through the sizing laser beam of the system 10 of FIG. 1. The x-axes 31, 32, and 33 represent time. The laser beam 18 generated orthogonally intersects the aerosol beam 15 with incident light from the laser beam 18 striking PMT 16. In turn, PMT 16 detects the light scattered by a particle 14 passing through the beam 18. The duration during which light is scattered indicates the traversal time of the particle 14 through the beam. The traversed time and known path length through the beam 18 is a function of the particle's velocity. From velocity, particle size can be estimated using a particle-velocity-to-size calibration means such as a calibration curve, as discussed further below with reference to FIG. 5.

The sizing laser 12 must produce a beam 18 having a path length of a known width or distance. In one embodiment, the sizing laser 12 forms a laser beam 18 that is square-shaped in cross section, with the top and bottom faces orthogonal to the plane of the particle beam 20 and focused at a point of intersection with the particle beam 20 to a known path length of one millimeter. Other cross-sectional shapes could be used, although shapes defining flat top and bottom surfaces orthogonal to the aerosol beam's path best facilitate clean particle entry and exit detection. A beam of a constant cross section is preferred. The sizing laser 12 can produce an appropriately shaped beam directly or by separate focus, such as lens or fiber optic cable. For example, a Diaguide SQ Series optical fiber, manufactured by Mitsubishi Cable America, Inc., Ann Arbor, Mich., can be used to shape a Blue Point 430/490 laser, described supra, into a one millimeter square beam.

Referring now to FIG. 3A, as the particle 14 intersects the sizing laser beam 18, scattered light is produced, which is detected by the PMT 16 and is converted into an electric pulse that is provided to a timing circuit (not shown). The point of initial intersection is denoted as time point $t_{enter}$. Referring now to FIG. 3B, depending on the data-sampling rate of the PMT 16, additional light scattering data points, $t_i$, are gathered as the particle travels through the beam 18. The data-sampling rate of the signal generated by the PMT 16 is set to provide the precision desired. For example, a particle 14 traveling within the aerosol beam 15 at 100 meters per second would traverse through a sizing laser beam 18 having a one-millimeter path length in ten microseconds. A sampling rate of 25 MHz yields approximately 250 data points $t_i$ of light scattering levels. Referring now to FIG. 3C, as the particle 14 exits the laser beam 18 generated by the sizing laser 12, a final data point of light scattering is detected, $t_{exit}$.

Light scattering duration by the particle 14 determines particle velocity. The difference in time between the particle 14 entering, $t_{enter}$, and exiting, $t_{exit}$, the sizing laser beam 18 and the known path length through the beam 18 can be used to determine the velocity of the particle 14, which can be expressed as:

$$t_A = t_{exit} - t_{enter} \quad (1)$$

where $t_A$, $t_{exit}$, and $t_{enter}$ are time in milliseconds. Particle velocity v can thus be expressed as:

$$v = d/t_A \quad (2)$$

where v is given in meters per second and d is the known path length of the beam in millimeters.

Detection of scattered light also allows synchronization of actuation of the desorption/ionization laser 17. Particle velocity can be used to time actuation of the desorption/ionization laser 17 of the mass spectrometer 13, so that the laser fires as the particle 14 enters the ion source region of the mass spectrometer 13. In a further embodiment, particle velocity is determined separately from ionization. Once the PMT 16 no longer detects scattered light, an electrical signal is sent by the timing circuit to fire the desorption/ionization laser 17 immediately, while velocity is separately determined and the two forms of data are synthesized post facto.

Higher concentrations of particles 14 within the aerosol beam increase the probability that two particles 14 will simultaneously reside within the particle sizing region, leading to inaccurate particle velocity and size determinations, as well as ambiguous spectral data from overlapping spectral patterns. The length over which particle velocity and size are determined is proportionate to the probability of particle simultaneity. Prior systems determine particle velocity and size over multi-centimeter particle sizing lengths. For example, the system disclosed in Prather et al., discussed supra, has a particle sizing region of six centimeters. A particle sizing region utilizing a single sizing laser beam 18 of one millimeter reduces the probability that two particles will simultaneously reside in the particle sizing region, providing increased sensitivity and throughput at higher particle concentrations.

Figure 4:
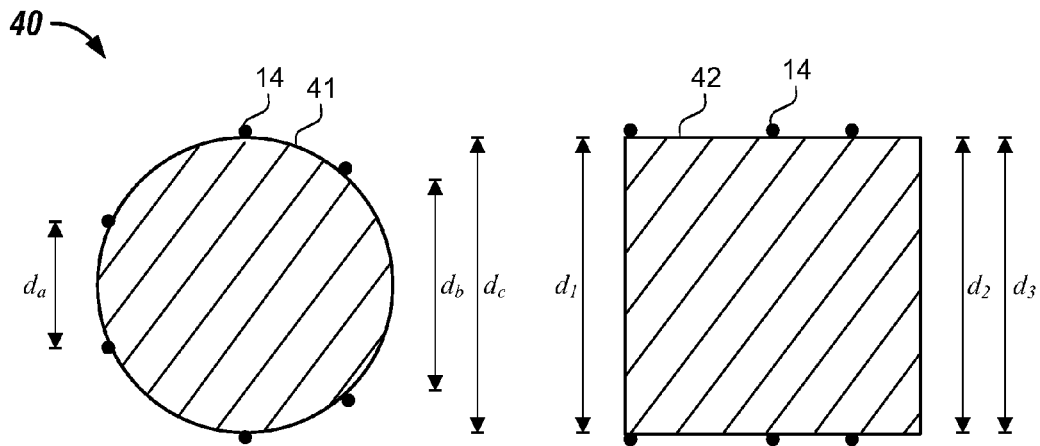

Particle size is estimated from particle velocity. FIG. 4 is a block diagram showing, respectively, path lengths through a circular shaped laser beam 41 and square shaped laser beam 42. Particle velocity is determined from the length of time a particle 14 needs to traverse the cross section of a laser beam 18. A known path length that the particle traverses is required for accurate velocity measurements, as discussed further above with reference to FIG. 3. A particle traveling a distance different from the known path length results in inaccurate particle velocity determinations. In general, the width of the particle beam 20 is larger than the width of the particles 14, though smaller than the width of the sizing laser beam 18. The particles 14 can be located anywhere within the width of the particle beam 20 as they travel along the axis of the beam 20 and can enter the sizing laser beam 18 at different points along the face of the beam 18.

A circular shaped laser beam 41 contains paths through the beam 41 of varying lengths. Although a circular shaped beam 41 can be focused to a known diameter, a particle 14 can enter the beam 41 at a position offline from the path along the diameter. For example, path lengths $d_a$, $d_b$, and $d_c$ are of different sizes, with $d_c > d_b > d_a$. A particle 14 traversing the beam 41 along $d_a$ will have a determined velocity higher than a particle traveling along $d_b$ or $d_c$, and higher than the actual velocity of the particle 14. The particle 14 would need to travel along the known path length $d_c$ for accurate particle velocity measurement. Any deviations by the particle 14 will result in inaccurate particle velocity measurement, inaccurate particle size estimation, and mistiming for firing the desorption/ionization laser 17.

On the other hand, a sizing laser beam 18 shaped so that a consistent path length occurs along the entire width of the beam results in accurate velocity determinations regardless of the path of the particle 14. For example, a square shaped beam 42 with two parallel faces oriented orthogonal to the particle beam 20 has about equidistant or constant path lengths, $d_1$, $d_2$, and $d_3$, through the beam 42. As used herein constant width of the beam means substantially constant, for example, a beam having variation in width of no more than about 10% of total width across the beam. The determined particle velocity will be substantially equal along any of the paths and consistent with the particle's true velocity.

Figure 5:
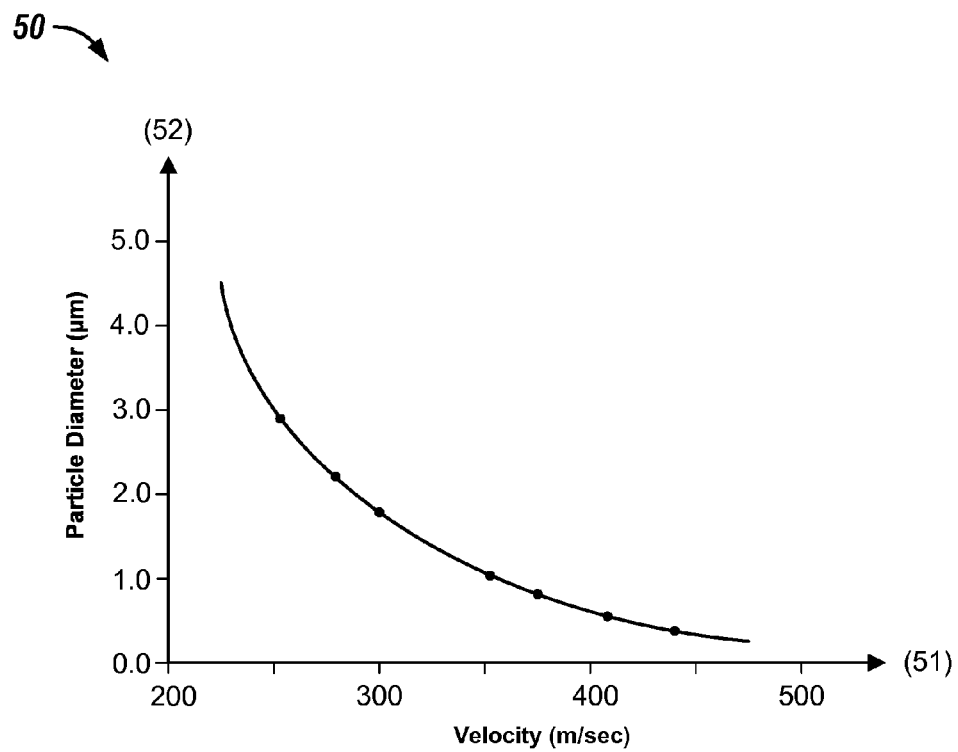

Particle size influences the particle's velocity through the system 10. FIG. 5 is a graph depicting an exemplary particle-size-to-particle-velocity calibration curve 50. The x-axis 51 represents aerosol particle velocities and the y-axis 32 represents particle diameters. In one embodiment, the curve 50 provides the velocities of benchmark aerosol particles 14 of known size. Benchmark aerosol particles can be formed, for example, using a vibrating orifice aerosol generator, such as Model 3450 Aerosol Generator, manufactured by TSI Inc., Shoreview, Minn. In a further embodiment, the curve 50 could be provided as reference data, without the need of benchmarking. The sizes of particles 14 of unknown size can then be determined from their observed velocity by comparison to the particle-size-to-particle-velocity curve 50. Other means of estimating particle velocity from particle size are possible, such as from a table or cross-reference list.

The system 10 can be used to analyze particles of unknown type in real time. FIG. 6 is a flow diagram showing a method 60 for determining the size and chemical composition of individual aerosol particles in accordance with one embodiment. When provided in portable form factor, the system 10 is transported to and installed on-site. Prior to operation, the system 10 is made ready, such as ensuring that the system electronics are calibrated, the aerosol beam pathway cleared, the lasers 12, 17 and the PMT 18 cleaned, and any prior specimen residue removed. Once operational, an aerosol sample is collected. The sample can be obtained from ambient open air sampling, from a contained sample, or by actively aerosolizing a test specimen. The aerosol is introduced into the system 10 through a conduit or pipe connecting the sample and the inlet 19 into the system 10. Initially, an aerosol beam 15, including particles 14, is generated (block 61) by the aerosol beam generator 11. The aerosol generator 11 is an aerodynamic focusing lens stack, as discussed above with reference to FIG. 1. The aerosol beam generator 11 accelerates the particles 14 to high velocity through supersonic expansion of the surrounding gas.

Next, the velocity and size of individual particles 14 are determined (block 62), as discussed further below with reference to FIG. 7. Briefly, particle velocity is determined from the residence time of a particle 14 within the beam 18 generated by the sizing laser 12. The velocity of the particle 14 is then used to determine particle size. Optionally, downstream, the particle 14 enters the mass spectrometer 13 and is ionized and desorbed by a pulsed laser 17 (block 63). Preferably, the mass spectrometer 13 is a dual-polarity time-of-flight mass spectrometer. The resulting ions are analyzed to determine the chemical composition of the particle 14 (block 64). Finally, the identity of the particle 14 is determined from the chemical composition and size of the particle 14 (block 65), such as disclosed in U.S. Pat. No. 7,260,483, issued to Gard et al., incorporated by reference.

Particle size is determined from the traversal time of the particle through a laser beam of known path length. FIG. 7 is a flow diagram showing the routine for determining the velocity and size of particles 14 for use in the method of FIG. 6. As a particle 14 within the particle beam 20 strikes (intersects) and travels through the laser beam 18 generated by the sizing laser 12, scattered light is produced. The scattered light is detected by the PMT 16. The scattered light is sampled at a rate sufficient to resolve the entry and exit time points of the particle 14. A sampling rate of 25 MHz is suitable for particles 14 traveling approximately 100 meters per second. Other sampling rates are applicable for lower or higher velocity particles 14. A time point is determined for particle entry into (block 71) and exit out of (block 72) the beam 18 generated by the sizing laser 12. Particle velocity is determined by the difference in the two time points and the known width of the sizing laser beam 18 (block 73). For example, a particle 14 with a traversal time of 2.5 microseconds through a beam 18 with a one-millimeter path length will have a determined velocity of 400 meters per second. Particle size is then determined from the velocity of the particle 14 (block 74) based on a size-to-velocity calibration curve unique to each apparatus or machine, as described above with reference to FIG. 5. For example, a particle 14 with a particle velocity of 400 meters per seconds corresponds to a particle size of 500 nanometers.

While the invention has been particularly shown and described as referenced to the embodiments thereof, those skilled in the art will understand that the foregoing and other changes in form and detail may be made therein without departing from the spirit and scope of the invention.

The invention claimed is:

1. Apparatus for determining the size of particles in an aerosol comprising:
   an aerosol beam generator that produces a focused particle stream and accelerates the particles to terminal velocities;
   a continuous wave sizing laser that produces a laser beam of constant width in the plane orthogonal to the focused particle stream so that a particle passing through the beam causes a detectable change in scattered light upon entering the beam and a detectable change in scattered light upon exiting the beam, the time being proportional to its velocity; and,
   an optical detection means that converts the scattered light upon entering and exiting the beam into an electric pulse that indicates time elapsed for the particle passing through the width of the sizing laser beam.

2. The apparatus of claim 1 wherein the there is also a particle analytical means for determination of particle composition disposed downstream the wave sizing laser.

3. The apparatus of claim 2 wherein the analytical means comprises:
   a pulsed desorption/ionization laser actuated by an electrical pulse from a timing circuit causing a laser beam to strike the particle, desorbing and ionizing it;
   and analytical means for determining the particle's chemical composition from the produced ions or other products of the desorption process.

4. The apparatus of claim 1 wherein a focusing means is positioned at the intersection of the sizing laser beam and the particle beam to direct scattered light to the optical detector means to avoid light being lost and undetected.

5. The apparatus of claim 1 wherein the sizing laser beam has multiple facets and is configured with two parallel faces of the beam intersecting the particle stream.

6. The apparatus of claim 2 wherein a focusing means is positioned at the intersection of the sizing laser beam and the particle beam to direct scattered light to the optical detector means to avoid light being lost and undetected.

7. The apparatus of claim 2 wherein the sizing laser beam has multiple facets and is configured with two parallel faces of the beam intersecting the particle stream.

8. The apparatus of claim 3 wherein the analytical means is a mass spectrometer.

9. The apparatus of claim 3 wherein the pulsed desorption/ionization laser is located so that its pulsed beam is positioned immediately below or partially overlaps the sizing laser beam.

10. The apparatus of claim 1 wherein the particle size is determined by computational means based upon the velocity of the particle, the velocity being proportional to the time elapsed for the particle to pass through the sizing laser beam, the width of the beam in the plane orthogonal to the particle stream and a calibration of size-to-velocity unique for the apparatus.

11. The apparatus of claim 3 wherein a desorption/ionization laser pulse beam is actuated by an electrical signal generated from a calculation of particle velocity determined by the duration of passage of the particle through the sizing laser beam and the distance from the bottom of the sizing laser beam to the path of the pulsed laser beam.

12. A method of determining the size of an aerosol particle comprising: introducing a particle-containing aerosol into the inlet of an aerosol beam generator that produces a focused particle stream and accelerates the particles to terminal velocities that are a function of particle size;
   passing the particle stream past a laser beam of a continuous wave sizing laser, the beam being of constant width in the plane orthogonal to the focused particle stream so that a particle passing through causes a detectable change in scattered light upon entering the beam and a detectable change in scattered light upon exiting the beam, the time being proportional to its velocity, and;
   generating an electric pulse from the scattered light upon entering and exiting the beam with an optical detection means that detects scattered light.

13. The method of claim 12 wherein the particle composition as determined by chemical analytical means.

14. The method of claim 13 wherein the particle analytical means comprises passing the particle beam through a pulsed desorption/ionization laser causing a laser beam to strike the particle producing spectra by particle desorption and ionization;
   and passing the spectra so produced into an analytical means for determining the particle chemical composition from the produced spectra.

15. The method of claim 14 wherein the analytical means is a mass spectrometer.

16. The method of claim 12 wherein the sizing laser beam has multiple facets and is configured with two parallel faces of the beam intersecting the particle stream.

17. The method of claim 12 wherein the aerosol beam generator is an aerodynamic focusing lens stack and a focusing means is positioned at the intersection of the sizing laser beam and the particle beam to direct scattered light to the optical detector means to avoid light being lost and undetected.

18. The method of claim 12 wherein a desorption/ionization laser pulse beam is actuated by an electrical signal generated from a calculation of particle velocity determined by the duration of passage of the particle through the sizing laser beam and the distance from the bottom of the sizing laser beam to the path of the pulsed laser beam.

* * * * *